United States Patent
Yeh

(10) Patent No.: US 11,521,763 B2
(45) Date of Patent: Dec. 6, 2022

(54) HEAT DISSIPATION STRUCTURE AND NEUTRON BEAM GENERATING DEVICE USING THE SAME

(71) Applicant: HERON NEUTRON MEDICAL CORP., Hsinchu County (TW)

(72) Inventor: Jyi-Tyan Yeh, Hsinchu County (TW)

(73) Assignee: HERON NEUTRON MEDICAL CORP., Hsinchu County (TW)

(*) Notice: Subject to any disclaimer, the term of this patent is extended or adjusted under 35 U.S.C. 154(b) by 0 days.

(21) Appl. No.: 16/840,447

(22) Filed: Apr. 5, 2020

(65) Prior Publication Data

US 2020/0365292 A1 Nov. 19, 2020

(30) Foreign Application Priority Data

May 16, 2019 (TW) ................. 108116969

(51) Int. Cl.
*G21G 4/02* (2006.01)
(52) U.S. Cl.
CPC ..................... *G21G 4/02* (2013.01)
(58) Field of Classification Search
CPC .. H05H 3/06; H05H 6/00; G21K 5/04; G21K 5/08; F28F 13/08; G21G 4/02; A61N 5/10; A61N 2005/002
See application file for complete search history.

(56) References Cited

U.S. PATENT DOCUMENTS

| | | | |
|---|---|---|---|
| 5,602,899 A * | 2/1997 | Larson | G01N 23/2273 378/143 |
| 5,898,261 A | 4/1999 | Barker | |
| 2018/0024599 A1 | 1/2018 | Sakata et al. | |

FOREIGN PATENT DOCUMENTS

| | | | |
|---|---|---|---|
| CN | 205584606 U | * | 9/2016 |
| CN | 205584606 U | | 9/2016 |
| JP | 40-030717 U | | 10/1965 |
| JP | H0396000 U | | 9/1991 |
| JP | 6-58398 U | | 8/1994 |

(Continued)

OTHER PUBLICATIONS

S. Halfon et al., "High-power liquid-lithium jet target for neutron production", Review of Scientific Instruments, AIP, Melville, NY, US, Dec. 13, 2013, vol. 84, No. 12., pp. 123507-1-123507-8.

(Continued)

*Primary Examiner* — Jack W Keith
*Assistant Examiner* — Joshua C Devorkin
(74) *Attorney, Agent, or Firm* — CKC & Partners Co., LLC

(57) ABSTRACT

A heat dissipation structure includes a housing. The housing has a bottom surface, a liquid inlet channel, a liquid outlet channel and a protruding portion. The liquid inlet channel and the liquid outlet channel are located at two opposite ends of the housing and above the bottom surface. The liquid inlet channel and the liquid outlet channel extend along a first direction. The protruding portion is located between the liquid inlet channel and the liquid outlet channel and above the bottom surface. The protruding portion protrudes towards a direction away from the bottom surface. The protruding portion has a protruding surface facing away from the bottom surface. A distance between the protruding surface and the bottom surface is increased first and then decreased along the first direction.

8 Claims, 4 Drawing Sheets

(56) References Cited

FOREIGN PATENT DOCUMENTS

| | | |
|---|---|---|
| JP | 06-058398 U | 8/1994 |
| JP | H0658398 U | 8/1994 |
| JP | 09-320795 A | 12/1997 |
| JP | 2002-289400 A | 10/2002 |
| JP | 2006-47115 A | 2/2006 |
| JP | 2009-193934 A | 8/2009 |
| JP | 2011-112413 A | 6/2011 |
| JP | 2018-021881 A | 2/2018 |
| TW | I442412 B | 6/2014 |
| TW | 201706008 A | 2/2017 |
| WO | WO-2017146205 A1 * | 8/2017 ............... H05H 3/06 |

OTHER PUBLICATIONS

T. Rinckel et al., "Target Performance at the Low Energy Neutron Source" (Physics Procedia 26 (2012) 168-177, 1875-3892, Published by Elsevier B.V. Selection and/or peer-review under responsibility of UCANS, DOI: 10.1016/j.phpro.2012.03.022).

Nigel R. Stevenson et al., "High current radioisotope production with solid target system" (DOI: 10.1109/PAC.1993.309565, Source: IEEE Xplore, Jun. 1993).

Jožef Čomor, "Solid Targetry for Compact Cyclotrons" (From :httpsinis.iaeaorgcollectionNCLCollectionStore_Public3912039120712.pdf, Sep. 19-21, 2004).

\* cited by examiner

HEAT DISSIPATION STRUCTURE AND NEUTRON BEAM GENERATING DEVICE USING THE SAME

RELATED APPLICATIONS

This application claims priority to Taiwanese Application Serial Number 108116969 filed May 16, 2019, which is herein incorporated by reference.

BACKGROUND

Technical Field

The present disclosure relates to heat dissipation structures and neutron beam generating devices using these heat dissipation structures.

Description of Related Art

To be specific, the principle of Boron Neutron Capture Therapy (BNCT) is as follows: boron-containing medicines are combined with tumor cells via blood circulation. A neutron beam is then used to irradiate the location of the tumor tissue as a center. Lithium and helium ions are then produced after boron absorbs the neutrons, which accurately destroy cancer cells without destroying other normal tissues.

For patients, boron neutron capture therapy causes only minimal damage and does not require surgery and anesthesia. Furthermore, in the treatment of brain tumors, if boron neutron capture therapy uses thermal neutrons with lower penetrating ability, the cranium of the patient has to be opened additionally. In contrast, if boron neutron capture therapy uses epithermal neutrons, the cranium of the patient is not required to be opened.

In this regard, the way of generating a neutron beam can be using a neutron beam generator of accelerator-type to bombard on a target with the ionic beam. However, in the process of generating a neutron beam, the target bombarded by the ionic beam may be unexpectedly damaged due to poor heat dissipation. Therefore, how to effectively solve the heat dissipation of the target in the process of generating neutron beams has become one of the directions in the research and development in the related fields.

SUMMARY

According to an embodiment of the present disclosure, a heat dissipation structure includes a housing. The housing has a bottom surface, a liquid inlet channel, a liquid outlet channel and a protruding portion. The liquid inlet channel and the liquid outlet channel are located at two opposite ends of the housing and above the bottom surface. The liquid inlet channel and the liquid outlet channel extend along a first direction. The protruding portion is located between the liquid inlet channel and the liquid outlet channel and above the bottom surface. The protruding portion protrudes towards a direction away from the bottom surface. The protruding portion has a protruding surface facing away from the bottom surface. A distance between the protruding surface and the bottom surface is increased first and then decreased along the first direction.

In one or more embodiments of the present disclosure, the protruding surface is a convex surface.

In one or more embodiments of the present disclosure, the protruding surface has a symmetric line extending along the first direction, and the protruding surface is symmetric relative to the symmetric line.

In one or more embodiments of the present disclosure, the distance between the protruding surface and the bottom surface is substantially the same along a second direction, and the second direction is perpendicular to the first direction.

In one or more embodiments of the present disclosure, the housing has a first opening, and the protruding portion extends and enters into the first opening.

In one or more embodiments of the present disclosure, the housing has a second opening. The second opening communicates with the first opening and is farther away from the protruding portion than the first opening. A dimension of the second opening is larger than a dimension of the first opening.

In one or more embodiments of the present disclosure, the housing has a pair of buffering grooves. The buffering grooves are respectively located at two opposite ends of the protruding portion and located between the liquid inlet channel and the liquid outlet channel.

In one or more embodiments of the present disclosure, a highest position of the protruding surface is higher than a highest position of the liquid inlet channel and the liquid outlet channel.

In one or more embodiments of the present disclosure, a lowest position of the protruding surface is higher than a highest position of the liquid inlet channel and the liquid outlet channel.

According to an embodiment of the present disclosure, a neutron beam generating device includes a heat dissipation structure as described above, a tubular body and an accelerator. The tubular body is disposed on the heat dissipation structure and has a channel. The accelerator is connected with the tubular body and is configured to emit an ionic beam towards a target disposed between the heat dissipation structure and the tubular body through the channel.

With regard to the configurations as described above, since the distance between the protruding surface of the protruding portion and the target disposed in the housing changes along the first direction, the flowing speed of the cooling fluid flowing through the protruding surface also changes. Therefore, the cooling fluid has a faster flowing speed with respect to the center of the target, leading to a better cooling effect at the center of the target. Through this mechanism, the heat dissipation structure is suitable to be applied in the neutron beam generating device.

BRIEF DESCRIPTION OF THE DRAWINGS

The disclosure can be more fully understood by reading the following detailed description of the embodiments, with reference made to the accompanying drawings as follows.

DETAILED DESCRIPTION

Figure 1:
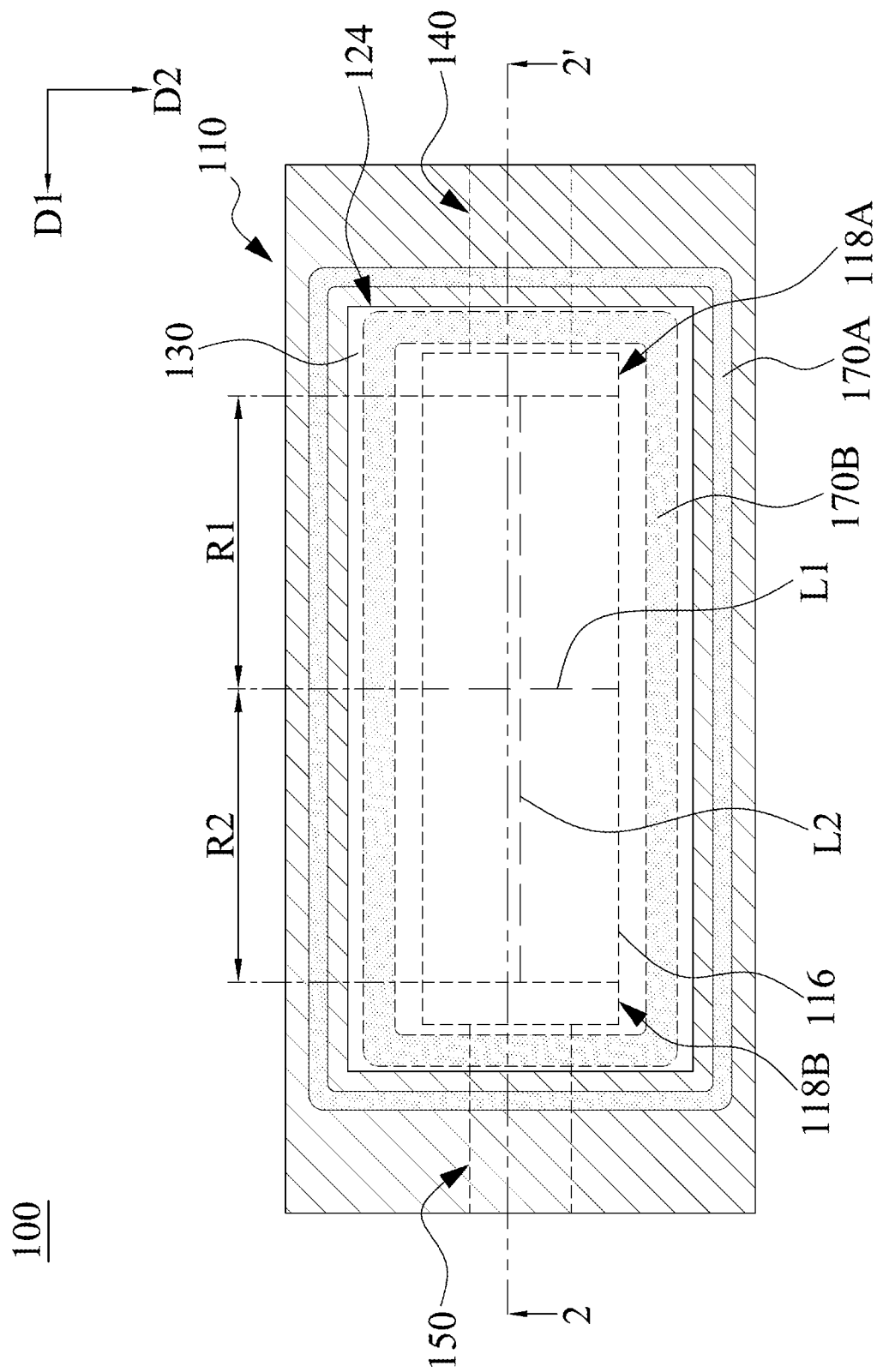
FIG. 1 is a top view of a heat dissipation structure according to some embodiments of the present disclosure.

Drawings will be used below to disclose embodiments of the present disclosure. For the sake of clear illustration, many practical details will be explained together in the description below. However, it is appreciated that the practical details should not be used to limit the claimed scope. In other words, in some embodiments of the present disclosure, the practical details are not essential. Moreover, for the sake of drawing simplification, some customary structures and elements in the drawings will be schematically shown in a simplified way. Wherever possible, the same reference numbers are used in the drawings and the description to refer to the same or like parts.

Unless otherwise defined, all terms (including technical and scientific terms) used herein have the same meanings as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

The heat dissipation structure of the present disclosure can control the flowing speed of the cooling fluid though the structural topography. Since the flowing speed of the cooling fluid and its cooling effect are related, different cooling effects can be provided according to different regions of the object to be cooled down (such as a target).

Figure 2:
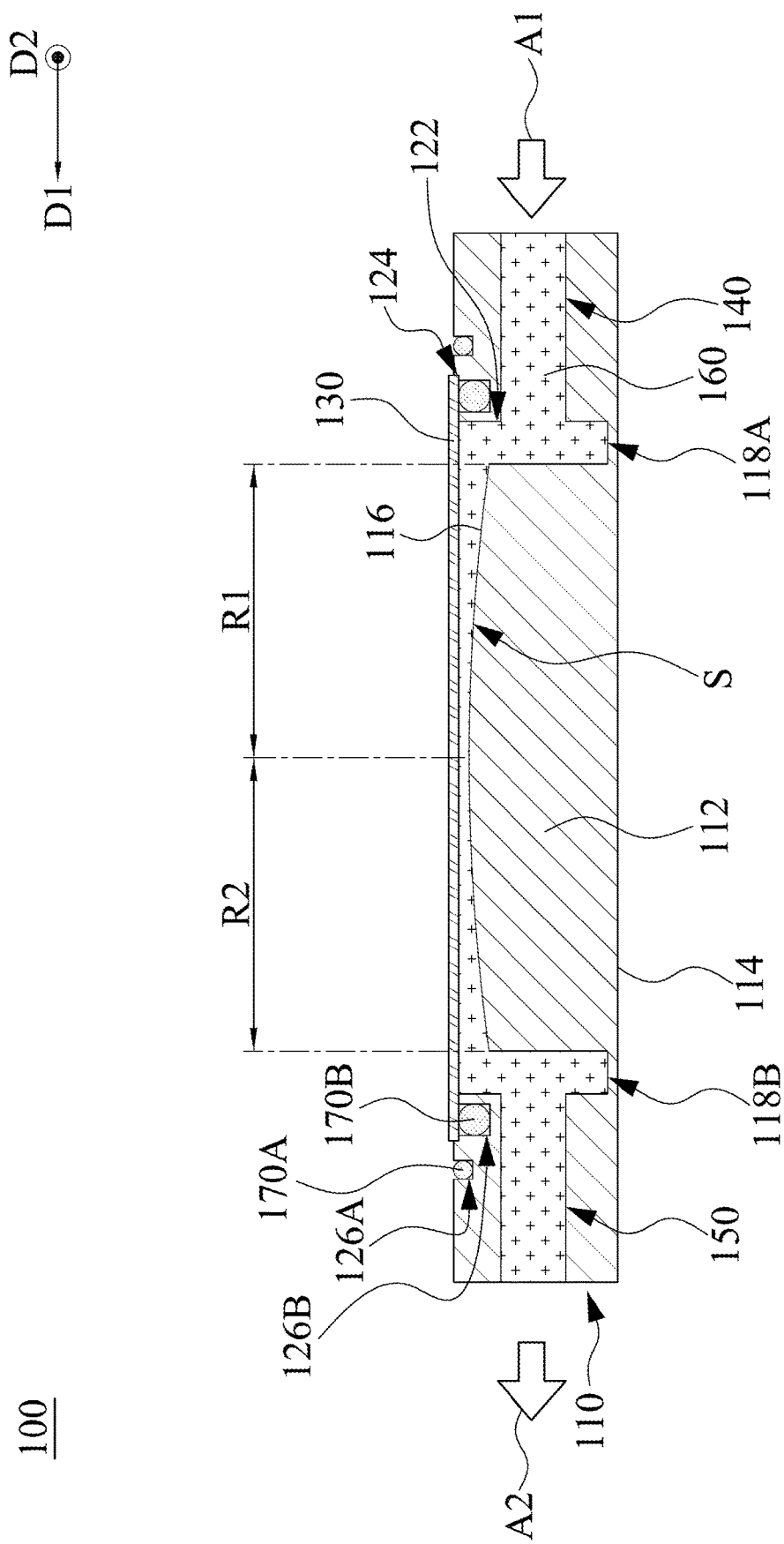
FIG. 2 is a cross-sectional view along the section line 2-2' of FIG. 1.

Reference is made to FIGS. 1-2. FIG. 1 is a top view of a heat dissipation structure 100 according to some embodiments of the present disclosure. FIG. 2 is a cross-sectional view along the section line 2-2' of FIG. 1. In order to prevent FIG. 1 from being over-complicated, the target 130 of FIG. 1 is not drawn with hatching lines as shown in FIG. 2. In addition, for the sake of convenient illustration, a first direction D1 and a second direction D2 are drawn in FIG. 1 and FIG. 2, in which the first direction D1 is different from the second direction D2. For example, the first direction D1 can be a transverse direction of FIG. 1, and the second direction D2 can be a longitudinal direction of FIG. 1, while the first direction D1 is perpendicular with the second direction D2.

The heat dissipation structure 100 includes a housing 110, in which the material of the housing 110 can be metal, such as aluminum. The housing 110 can be integrally formed and can also be formed from assembly. The housing 110 has a protruding portion 112, a bottom surface 114, a first opening 122, a second opening 124, a liquid inlet channel 140 and a liquid outlet channel 150, in which the bottom surface 114 can be regarded as the bottommost surface of the housing 110. The first opening 122 and the second opening 124 are communicated with each other and are both located above the bottom surface 114. The second opening 124 is farther away from the bottom surface 114 than the first opening 122. The housing 110 can be used to carry a target 130, in which the target 130 can be of a plate-shaped target. A dimension of the second opening 124 can be larger than a dimension of the first opening 122. Through this difference in dimensions, the positioning of the target 130 can be facilitated. In this regard, the dimension as mentioned above can be the length or the width. Taking FIG. 2 as an example, the width of the second opening 124 is larger than the width of the first opening 122. Moreover, since the housing 110 has the first opening 122, after the target 130 is disposed on the housing 110, the target 130 and the housing 110 can together form an accommodation space S therebetween.

The liquid inlet channel 140 and the liquid outlet channel 150 are located at two opposite ends of the housing 110 and also located above the bottom surface 114. The liquid inlet channel 140 and the liquid outlet channel 150 can extend along the same direction, such as the first direction D1, and respectively connect with the accommodation space S. In some embodiments, a pressure device (not shown) can be used to deliver a cooling fluid 160 from the liquid inlet channel 140 to the inside of the heat dissipation structure 100, as shown by the arrow A1, such that cooling fluid 160 can flow through the accommodation space S and contact with the target 130, providing a cooling effect to the target 130. Afterwards, the cooling fluid 160 can leave from the heat dissipation structure 100 through the liquid outlet channel 150, as shown by the arrow A2.

The protruding portion 112 is located between the liquid inlet channel 140 and the liquid outlet channel 150, and is also located above the bottom surface 114. The protruding portion 112 protrudes towards a direction away from the bottom surface 114.

The protruding portion 112 extends by protruding and enters into the first opening 122. The second opening 124 is farther away from the protruding portion 112 than the first opening 122. The protruding portion 112 has a protruding surface 116 facing away from the bottom surface 114. In other words, the protruding surface 116 faces to the first opening 122 and the second opening 124. A distance between the protruding surface 116 and the bottom surface 114 is increased first and then decreased along the first direction D1. For example, the protruding surface 116 is a convex surface, such that the distance between the protruding surface 116 and the bottom surface 114 is increased first and then decreased along the first direction D1.

Through the design of the distance between the protruding surface 116 and the bottom surface 114 to be increased first and then decreased, after the target 130 is disposed on the housing 110, the distance between the target 130 and the protruding surface 116 of the housing 110 is decreased first and then increased. Through this configuration, when the cooling fluid 160 flows through the protruding surface 116 in a direction from the liquid inlet channel 140 to the liquid outlet channel 150, the flowing speed of the cooling fluid 160 changes with the change of the distance between the target 130 and the protruding surface 116 of the housing 110.

To be specific, with regard to the cooling fluid 160 flowing through the former half region R1 of the protruding surface 116 in the direction from the liquid inlet channel 140 to the liquid outlet channel 150, since the distance between the target 130 and the protruding surface 116 of the housing 110 is gradually decreased, the flowing speed of the cooling fluid 160 is gradually increased. In this regard, since the flowing speed of the cooling fluid 160 is directly proportional to the cooling effect the cooling fluid 160 can provide, the increase in the cooling speed of the cooling fluid 160 can increase the cooling effect. In other words, within the former half region R1 of the protruding surface 116, the cooling effect provided by the cooling fluid 160 gradually increases with the protruding terrain of the protruding surface 116.

Subsequently, with regard to the cooling fluid 160 flowing through the latter half region R2 of the protruding surface 116 in the direction from the liquid inlet channel 140 to the liquid outlet channel 150, the distance between the target 130 and the protruding surface 116 of the housing 110 is gradually increased such that the flowing speed of the cooling fluid 160 is gradually decreased. Since the flowing speed of the cooling fluid 160 is decreased, the pressure exerting on the center of the target 130 by the cooling fluid 160 is decreased, such that the stress produced on the target 130 is decreased.

In other words, the heat dissipation structure 100 makes the cooling fluid 160 have a faster flowing speed with respect to the center of the target 130, and leads to a better cooling effect at the center of the target 130 by the cooling fluid 160. It also means that the cooling effect provided by the cooling fluid 160 to the target 130 is decreased gradually from the highest position of the protruding surface 116 to the liquid inlet channel 140/the liquid outlet channel 150. Through this mechanism, the heat dissipation structure 100 is suitable to carry out heat dissipation to the target 130 with heat distribution in the pattern of "gradual decrease to the two sides from the center", in which "gradual decrease to the two sides from the center" can be, for example, of Gaussian distribution, normal distribution or bell-shaped distribution.

On the contrary, if the distance between the protruding surface 116 and the bottom surface 114 is not structurally designed to be first increased and then decreased, i.e., under the condition that the gap of the channel of the cooling fluid is constant, the flowing speed of the cooling fluid from the liquid inlet channel to the liquid outlet channel is constant. Moreover, when the overall flow rate remains unchanged, the smaller the width of the constant gap, the faster the flowing speed will be, causing a larger pressure gradient. Thus, the structure with a constant gap of the channel is not suitable to carry out heat dissipation to the target with heat distribution in the pattern of "gradual decrease to the two sides from the center".

On the other hand, the magnitude of the gradual increase and the magnitude of the gradual decrease of the protruding surface 116 can be designed to be the same or different, in order to facilitate the control of the flowing direction of the cooling fluid 160. To be specific, the magnitude of the gradual increase and the magnitude of the gradual decrease of the protruding surface 116 can be equal. Under such condition, the protruding surface 116 has a first symmetric line L1 (as shown in FIG. 1) extending along the second direction D2, and the protruding surface 116 is symmetric relative to the first symmetric line L1. However, this does not intend to limit the present disclosure. In other embodiments, the magnitude of the gradual increase and the magnitude of the gradual decrease of the protruding surface 116 are different from each other. For example, a distance between the an end of the protruding surface 116 close to the liquid inlet channel 140 and the bottom surface 114 can be larger than a distance between the an end of the protruding surface 116 close to the liquid outlet channel 150 and the bottom surface 114, such that the magnitude of the gradual increase of the protruding surface 116 is less than the magnitude of the gradual decrease.

The protruding surface 116 can also be designed to have a protruding change in only the first direction D1, in order to facilitate the control of the flowing direction of the cooling fluid 160. For example, the accelerating effect of the cooling fluid 160 in the direction from the liquid inlet channel 140 to the liquid outlet channel 150 is larger than the accelerating effect in other directions. To be specific, the distance between the protruding surface 116 and the bottom surface 114 is substantially the same along the second direction D2. Under such condition, the protruding surface 116 has a second symmetric line L2 (as shown in FIG. 1) extending along the first direction D1, and the protruding surface 116 is symmetric relative to the second symmetric line L2. Moreover, the housing 110 can have a pair of buffering grooves 118A & 118B. The buffering grooves 118A & 118B are respectively located at two opposite ends of the protruding portion 112 and are located between the liquid inlet channel 140 and the liquid outlet channel 150. The lowest position and the highest position of the protruding surface 116 is higher than the highest position of the liquid inlet channel 140 and the liquid outlet channel 150.

Through this mechanism, when the cooling fluid 160 flows from the liquid inlet channel 140 into the heat dissipation structure 100, the cooling fluid 160 can be prevented from entering into the accommodation space S between the target 130 and the protruding surface 116. To be specific, the cooling fluid 160 flowing from the liquid inlet channel 140 into the heat dissipation structure 100 flows into the accommodation space S between the target 130 and the protruding surface 116 after at least two occasions of direction changes, facilitating the control of the flowing speed of the cooling fluid 160. On the other hand, the heat dissipation structure 100 can further includes two sealing gasket 170A & 170B, in which the housing 110 can have two grooves 126A & 126B. The sealing gasket 170A & 170B are respectively disposed with the grooves 126A & 126B. The sealing gasket 170A & 170B can provide air tightness and water-proof effect.

In some embodiments, the difference in value between the shortest distance between the protruding surface 116 and the target 130 and the longest distance between the protruding surface 116 and the target 130 can be within 0.3 mm and 0.7 mm. For example, the shortest distance between the protruding surface 116 and the target 130 can be 0.5 mm, and the longest distance between the protruding surface 116 and the target 130 can be 1 mm. In some embodiments, the length of the protruding surface 116 in FIG. 1A along the first direction D1 can be within 160 mm and 200 mm, and the length of the protruding surface 116 in FIG. 1A along the second direction D2 can be within 60 mm and 70 mm. In some embodiments, the distances between the bottom of the buffering grooves 118A & 1186 and the target 130 can be within 25 mm and 35 mm, and the widths of the buffering grooves 118A & 118B can be within 8 mm and 12 mm. In some embodiments, the liquid inlet channel 140 and the liquid outlet channel 150 can be circular channels, and the diameters of these circular channels can be within 18 mm and 22 mm.

As mentioned above, since the heat dissipation structure 100 is suitable to carry out heat dissipation to the target 130 with heat distribution in the pattern of gradual decrease to the two sides from the center, the heat dissipation structure 100 is suitable to be applied to device which would cause the target 130 to have this pattern of heat distribution during operation, such as a neutron beam generating device. A neutron beam generating device is taken as an example to be described below.

Figure 3:
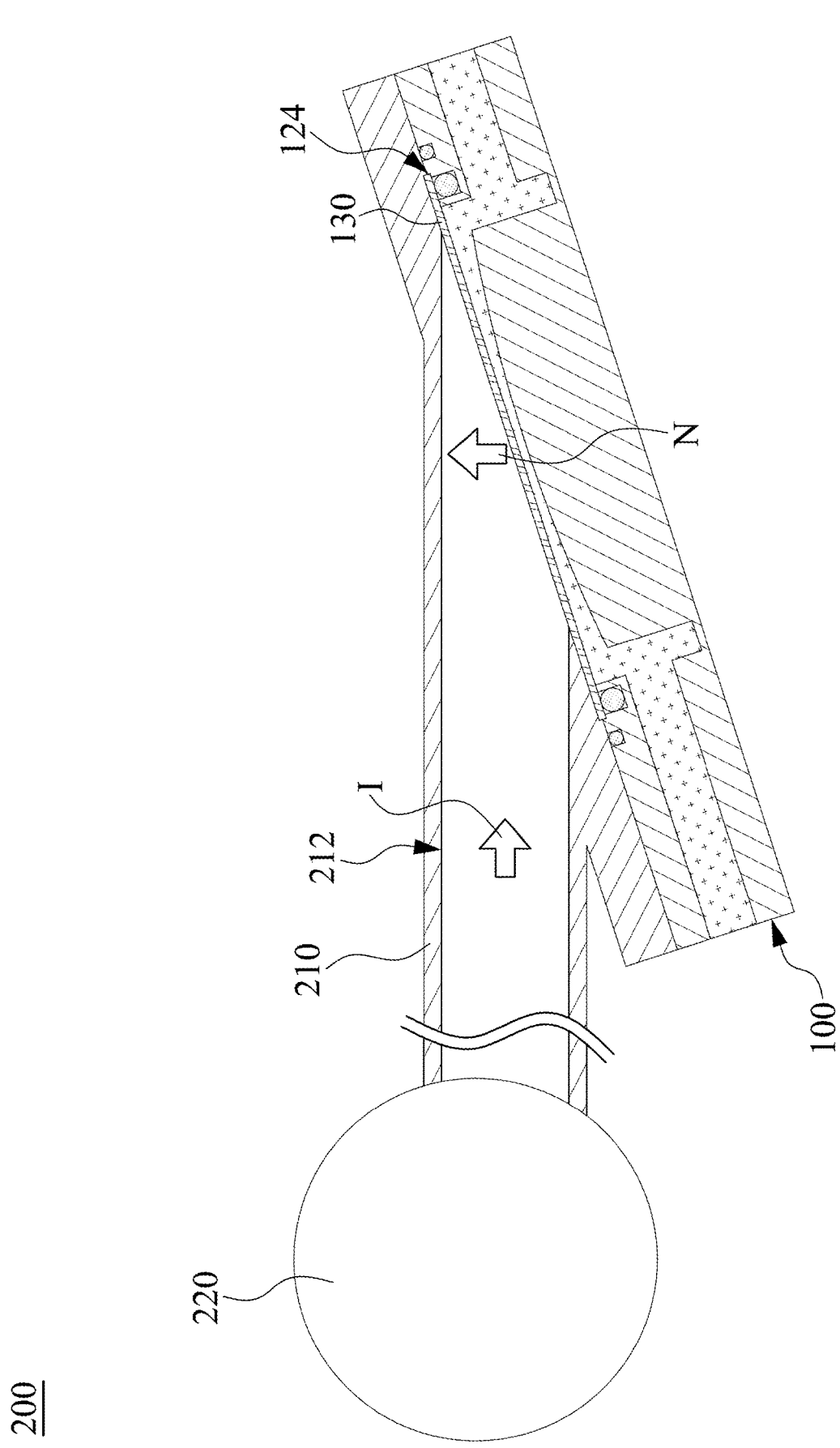
FIG. 3 is a schematic view of a neutron beam generating device according to some embodiments of the present disclosure.

Reference is made to FIG. 3. FIG. 3 is a schematic view of a neutron beam generating device 200 according to some embodiments of the present disclosure. In order to prevent FIG. 3 from being over-complicated, the proportional relation between each of the layers shown in FIG. 3 is not necessary to be the same as the actual proportion. The structures drawn are used to assist for description only, but are not intended to limit the relation of the relative positions of the layers in the structure. In other embodiments, some of the layers can be omitted while other layers can be added.

As shown in FIG. 3, a neutron beam generating device 200 includes the heat dissipation structure 100, a tubular body 210 and an accelerator 220. The tubular body 210 is disposed on the heat dissipation structure 100. The target 130 can be disposed between the heat dissipation 100 and the tubular body 210. To be specific, the target 130 can be secured inside the second opening 124 of the housing 110 of the heat dissipation structure 100. In some embodiments, the material of the target 130 can include beryllium (Be), and the thickness of the target 130 can be within 1.5 mm and 2.5 mm. The tubular body 210 has a channel 212, and the accelerator 220 can be connected with the tubular body 210. The accelerator 220 can be configured to emit an ionic beam I towards the target 130 through the channel 212. In other words, the ionic beam I produced from the accelerator 220 can pass through the channel 212 and bombard on the target 130, such that a neutron beam N suitable to be used in boron neutron capture therapy can be stimulated.

Figure 4:
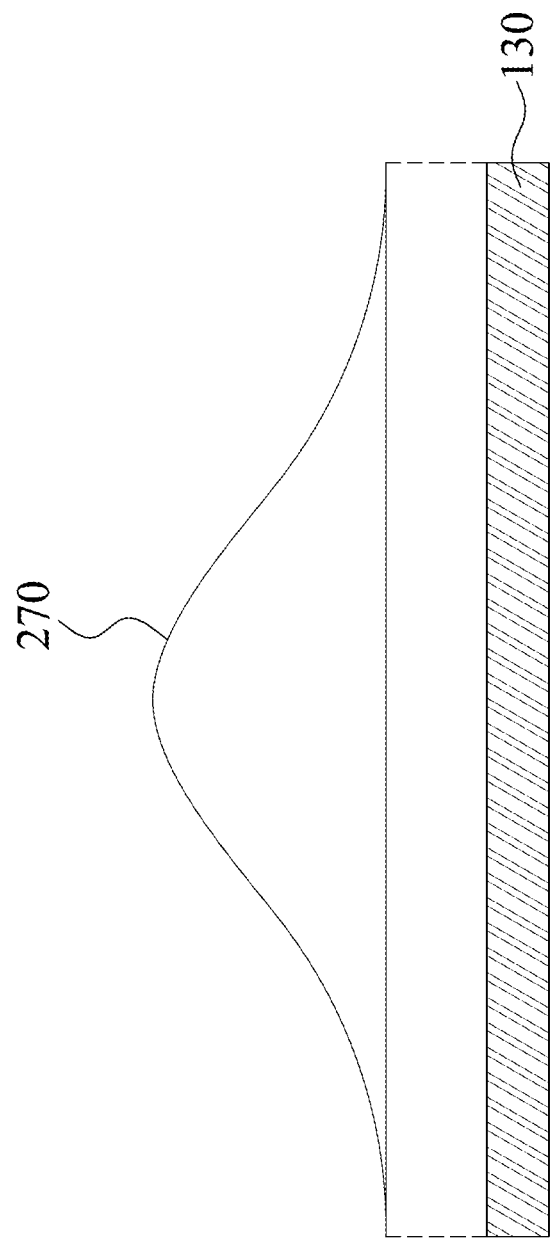
FIG. 4 is a schematic view of heat distribution of the target of FIG. 3.

Reference is made to both FIG. 3 and FIG. 4. FIG. 4 is a schematic view of heat distribution of the target 130 of FIG. 3. When the accelerator 220 emits the ionic beam I towards the target 130 through the channel 212, the density distribution of the ionic beam I emitted is in the form of Gaussian distribution, just like the heat distribution 270 as shown in FIG. 4. In other words, the target 130 can be regarded as a heat source with Gaussian distribution. Since the heat dissipation structure 100 is suitable to carry out heat dissipation to this kind of heat source, the heat dissipation structure 100 can prevent the neutron beam generating device 200 from experiencing unexpected damage during operation, such as the burst of the target 130 due to overheat.

In conclusion, the heat dissipation structure in the present disclosure includes housing. The housing has the protruding portion, and the distance between the protruding surface of the protruding portion and the target disposed in the housing changes along the first direction, such that the flowing speed of the cooling fluid flowing through the protruding surface also changes. Therefore, the cooling fluid has a faster flowing speed with respect to the center of the target, leading to a better cooling effect at the center of the target. Through this mechanism, the heat dissipation structure is suitable to be applied in the neutron beam generating device.

Although the present disclosure has been described in considerable detail with reference to certain embodiments thereof, other embodiments are possible. Therefore, the spirit and scope of the appended claims should not be limited to the description of the embodiments contained herein.

It will be apparent to the person having ordinary skill in the art that various modifications and variations can be made to the structure of the present disclosure without departing from the scope or spirit of the present disclosure. In view of the foregoing, it is intended that the present disclosure cover modifications and variations of the present disclosure provided they fall within the scope of the following claims.

What is claimed is:

1. A heat dissipation structure, comprising:
a housing having a bottom surface, a liquid inlet channel, a liquid outlet channel and a protruding portion, wherein the liquid inlet channel and the liquid outlet channel are located at two opposite ends of the housing and above the bottom surface, and the liquid inlet channel and the liquid outlet channel extend along a first direction, the protruding portion is located between the liquid inlet channel and the liquid outlet channel and above the bottom surface, the protruding portion protrudes away from the bottom surface, the protruding portion has a protruding surface facing away from the bottom surface, a highest position of the protruding surface is higher than a highest position of the liquid inlet channel and the liquid outlet channel, the protruding surface has a former half region, a latter half region and a first symmetric line, the first symmetric line extends along a second direction perpendicular to the first direction, the former half region and the latter half region are symmetric with each other relative to the first symmetric line and directly connected with each other at the first symmetric line along the first direction, a first distance between the protruding surface and the bottom surface is continuously increased first throughout the former half region and then continuously decreased throughout the latter half region along the first direction, and the protruding surface is a convex surface curved along the first direction, the housing is configured to support a target, a second distance between the target and the protruding surface along a third direction perpendicular to the target is continuously decreased first throughout the former half region and then continuously increased throughout the latter half region along the first direction.

2. The heat dissipation structure of claim 1, wherein the protruding surface has a second symmetric line extending along the first direction, and the protruding surface is symmetric relative to the second symmetric line.

3. The heat dissipation structure of claim 1, wherein the housing has a pair of buffering grooves respectively located at two opposite ends of the protruding portion and located between the liquid inlet channel and the liquid outlet channel.

4. The heat dissipation structure of claim 1, wherein a lowest position of the protruding surface is higher than the highest position of the liquid inlet channel and the liquid outlet channel.

5. A neutron beam generating device, comprising:
the heat dissipation structure of claim 1;
a tubular body disposed on the heat dissipation structure and having a channel; and
an accelerator connected with the tubular body and configured to emit an ionic beam towards the target disposed between the heat dissipation structure and the tubular body through the channel.

6. A neutron beam generating device, comprising:
the heat dissipation structure of claim 2;
a tubular body disposed on the heat dissipation structure and having a channel; and
an accelerator connected with the tubular body and configured to emit an ionic beam towards the target disposed between the heat dissipation structure and the tubular body through the channel.

7. A neutron beam generating device, comprising:
the heat dissipation structure of claim 3;
a tubular body disposed on the heat dissipation structure and having a channel; and
an accelerator connected with the tubular body and configured to emit an ionic beam towards the target disposed between the heat dissipation structure and the tubular body through the channel.

8. A neutron beam generating device, comprising:
the heat dissipation structure of claim 4;
a tubular body disposed on the heat dissipation structure and having a channel; and
an accelerator connected with the tubular body and configured to emit an ionic beam towards the target disposed between the heat dissipation structure and the tubular body through the channel.

* * * * *